United States Patent
Stinson et al.

(10) Patent No.: US 9,603,728 B2
(45) Date of Patent: *Mar. 28, 2017

(54) BIOERODIBLE MAGNESIUM ALLOY MICROSTRUCTURES FOR ENDOPROSTHESES

(71) Applicant: Boston Scientific Scimed, Inc., Maple Grove, MN (US)

(72) Inventors: Jonathan S. Stinson, Plymouth, MN (US); Dennis A. Boismier, Shorewood, MN (US); Jacob Drew Edick, Minneapolis, MN (US); Torsten Scheuermann, Munich (DE); Louis Toth, Rogers, MN (US); Jan Webber, Maple Grove, MN (US); Charles Deng, Chanhassen, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/178,869

(22) Filed: Feb. 12, 2014

(65) Prior Publication Data

US 2014/0236284 A1    Aug. 21, 2014

Related U.S. Application Data

(60) Provisional application No. 61/765,412, filed on Feb. 15, 2013.

(51) Int. Cl.
*A61L 27/58*    (2006.01)
*A61F 2/82*    (2013.01)
(Continued)

(52) U.S. Cl.
CPC .............. *A61F 2/82* (2013.01); *A61L 31/022* (2013.01); *A61L 31/14* (2013.01); *A61L 31/148* (2013.01); *C22C 23/02* (2013.01); *C22F 1/06* (2013.01)

(58) Field of Classification Search
CPC .................................. C22C 23/02; A61F 2/82
(Continued)

(56) References Cited

U.S. PATENT DOCUMENTS 4,542,539 A    9/1985   Rowe, Jr. et al.
5,769,884 A    6/1998   Solovay
(Continued)

FOREIGN PATENT DOCUMENTS

EP    1548138    6/2005
EP    2210625    7/2010
(Continued)

OTHER PUBLICATIONS

Chakkedath, J. B. et al., "The Effect of Nd on the Tension and Compression Deformation Behavior of Extruded Mg-1 Mn (wt pct) at Temperatures Between 298 K and 523 K (25 degrees C and 250 degrees C)," Metallurgical and Materials Transactions A, vol. 45A, Jul. 2014, pp. 3254-3274 (21 pages).
(Continued)

*Primary Examiner* — Jie Yang
(74) *Attorney, Agent, or Firm* — Pauly, DeVries Smith & Deffner, L.L.C.

(57) ABSTRACT

A bioerodible endoprosthesis includes a bioerodible magnesium alloy. The bioerodible magnesium alloy has a microstructure including equiaxed Mg-rich solid solution-phase grains having an average grain diameter of less than or equal to 5 microns and second-phase precipitates in grain boundaries between the equiaxed Mg-rich solid solution-phase grains. The beta-phase precipitates have an average longest
(Continued)

dimension of 0.5 micron or less. The microstructure can be produced by one or more equal-channel high-strain processes.

18 Claims, 6 Drawing Sheets

(51) Int. Cl.
    *A61L 31/02*     (2006.01)
    *C22C 23/02*     (2006.01)
    *C22F 1/06*     (2006.01)
    *A61L 31/14*     (2006.01)

(58) Field of Classification Search
    USPC ........................................................ 148/667
    See application file for complete search history.

(56) References Cited

U.S. PATENT DOCUMENTS

| | | | |
|---|---|---|---|
| 5,843,172 | A | 12/1998 | Yan et al. |
| 6,240,616 | B1 | 6/2001 | Yan et al. |
| 6,287,332 | B1 | 9/2001 | Bolz et al. |
| 6,290,721 | B1 | 9/2001 | Heath |
| 6,521,061 | B1 | 2/2003 | Fukunaga et al. |
| 6,716,444 | B1 | 4/2004 | Castro et al. |
| 6,723,120 | B2 | 4/2004 | Yan et al. |
| 6,770,086 | B1 | 8/2004 | Girton |
| 6,908,516 | B2 | 6/2005 | Weidemann et al. |
| 8,052,744 | B2 | 11/2011 | Girton et al. |
| 8,202,477 | B2 * | 6/2012 | Papirov ................ A61L 29/02 420/402 |
| 8,449,603 | B2 | 5/2013 | Weber et al. |
| 8,840,660 | B2 | 9/2014 | Weber |
| 9,522,220 | B2 | 12/2016 | Edick |
| 2002/0004060 | A1 | 1/2002 | Heublein et al. |
| 2002/0197178 | A1 | 12/2002 | Yan et al. |
| 2004/0039438 | A1 | 2/2004 | Alt et al. |
| 2004/0220660 | A1 | 11/2004 | Shanley et al. |
| 2004/0267354 | A1 | 12/2004 | Ringeisen et al. |
| 2005/0119723 | A1 | 6/2005 | Peacock et al. |
| 2005/0192657 | A1 | 9/2005 | Colen et al. |
| 2005/0261760 | A1 | 11/2005 | Weber et al. |
| 2005/0283229 | A1 | 12/2005 | Dugan et al. |
| 2006/0193886 | A1 | 8/2006 | Owens et al. |
| 2006/0199876 | A1 | 9/2006 | Troczynski et al. |
| 2006/0229711 | A1 | 10/2006 | Yan et al. |
| 2006/0271168 | A1 | 11/2006 | Kleine et al. |
| 2007/0264303 | A1 | 11/2007 | Atanasoska et al. |
| 2008/0004691 | A1 | 1/2008 | Weber et al. |
| 2008/0031765 | A1 | 2/2008 | Gerold et al. |
| 2008/0082162 | A1 | 4/2008 | Boismier et al. |
| 2008/0109072 | A1 | 5/2008 | Girton et al. |
| 2008/0195189 | A1 | 8/2008 | Asgari et al. |
| 2009/0081313 | A1 * | 3/2009 | Aghion ................ A61L 27/047 424/641 |
| 2009/0088834 | A1 | 4/2009 | Wang |
| 2009/0192595 | A1 | 7/2009 | Kawamura et al. |
| 2010/0262222 | A1 | 10/2010 | Weber et al. |
| 2011/0172724 | A1 * | 7/2011 | Hort ................ A61L 24/0063 606/86 R |
| 2012/0046734 | A1 | 2/2012 | Girton et al. |
| 2012/0053674 | A1 | 3/2012 | Boismier et al. |
| 2012/0059455 | A1 | 3/2012 | Weber et al. |
| 2012/0215301 | A1 * | 8/2012 | Papirov ................ A61L 27/047 623/1.42 |
| 2013/0039805 | A1 | 2/2013 | Somekawa et al. |
| 2014/0236284 | A1 | 8/2014 | Stinson et al. |
| 2015/0066135 | A1 * | 3/2015 | Weber ................ A61F 2/82 623/1.38 |
| 2015/0157767 | A1 * | 6/2015 | Edick ................ C22C 23/04 623/1.15 |
| 2016/0263288 | A1 | 9/2016 | Edick et al. |

FOREIGN PATENT DOCUMENTS

| | | |
|---|---|---|
| EP | 2959925 | 12/2015 |
| EP | 2613817 | 3/2016 |
| JP | 2016509875 | 4/2016 |
| WO | 2007082147 | 7/2007 |
| WO | 2008034013 | 3/2008 |
| WO | 2008034066 | 3/2008 |
| WO | 2008091835 | 7/2008 |
| WO | 2009036140 | 3/2009 |
| WO | 2009137786 | 11/2009 |
| WO | 2010003003 | 1/2010 |
| WO | 2010093244 | 8/2010 |
| WO | 2009152153 | 9/2010 |
| WO | 2010014612 | 10/2010 |
| WO | 2011011531 | 3/2011 |
| WO | 2010040084 | 6/2011 |
| WO | 2011081958 | 7/2011 |
| WO | 2011117298 | 9/2011 |
| WO | 2012033637 | 3/2012 |
| WO | 2014126958 | 8/2014 |
| WO | 2014126958 | 11/2014 |
| WO | 2015066181 | 5/2015 |
| WO | 2016145368 | 9/2016 |

OTHER PUBLICATIONS

Cho, S. S. et al., "Structure and properties of rapidly solidified Mg—Al alloys," Journal of Materials Science 34 (1999) 4311-4320, 10 pages.
"Communication Pursuant to Article 94(3) EPC," for European Patent Application No. 15176192.1, mailed Nov. 25, 2015 (4 pages).
"Communication Pursuant to Rules 161(1) and 162 EPC," for European Patent Application No. 14706247.5, mailed Oct. 30, 2015 (2 pages).
"Final Office Action," for U.S. Appl. No. 13/284,467, mailed Jan. 25, 2016 (16 pages).
"Final Office Action," for U.S. Appl. No. 14/178,869, mailed Apr. 5, 2016 (16 pages).
"International Preliminary Report on Patentability," for PCT Application No. PCT/US2014/062902, mailed May 12, 2016 (9 pages).
"International Preliminary Report on Patentability," for PCT/US2007/078417 mailed Mar. 17, 2009 (7 pages).
"International Preliminary Report on Patentability," for PCT/US2009/046750 mailed Dec. 23, 2010 (7 pages).
"International Preliminary Report on Patentability," for PCT/US2009/059424 mailed May 5, 2011 (7 pages).
"International Preliminary Report on Patentability," for PCT/US2014/015932, mailed Aug. 18, 2015 (9 pages).
"International Search Report & Written Opinion," for PCT/US2007/078417, mailed Jan. 22, 2009 (14 pages).
"International Search Report & Written Opinion," for PCT/US2014/015932, mailed May 22, 2014 (11 pages).
"International Search Report & Written Opinion," for PCT/US2014/062902, mailed Feb. 18, 2015 (12 pages).
"International Search Report and Written Opinion," for PCT Application No. PCT/US2016/022110, mailed May 24, 2016 (12 pages).
"International Search Report," for PCT/US2009/046750 mailed Jul. 20, 2010 (4 pages).
"International Search Report," for PCT/US2009059424 mailed Apr. 21, 2011 (4 pages).
Joshi, S. et al., "High Shear Deformation to Produce High Strength and Energy Absorption in MG Alloys," Editor Martyn Alderman et al., Magnesium Technology 2014, TMS (The Minerals, Metals, and Materials Society), 2014, Wiley Publishers, pp. 83-88.
Khan, Mohammad N. "Solidification study of commercial magnesium alloys," Master's Thesis, Concordia University, Montreal, Quebec, Canada, Oct. 2009 (105 pages).
Kim, et al., "Continuous Casting of Magnesium Alloy Billet Using Electromagnetic Techniques," Materials Science Forum vols. 654-656, Nie and Morton, Jun. 2010 pp. 787-790.
Milner, F. et al., "Microstructural Evolution and Its Relationship to the Mechanical Properties of Mg AZ31B Friction Stir Back (56) References Cited

OTHER PUBLICATIONS

Extruded Tubes," Editor Martyn Alderman et al., Magnesium Technology 2014, TMS (The Minerals, Metals, and Materials Society), 2014, Wiley Publishers, pp. 263-268.
"Non-Final Office Action," for U.S. Appl. No. 13/284,467 mailed Aug. 6, 2015 (11 pages).
"Office Action," for U.S. Appl. No. 14/178,869 mailed Oct. 19, 2015 (9 pages).
Park, Won-Wook et al., "Microstructural change and precipitation hardening in melt-spun Mg-X-Ca alloys," Science and Technology of Advanced Materials (2001), 2:1 pp. 73-78.
"Response to Communication Pursuant to Article 94(3) EPC," for European Patent Application No. 15176192.1, filed with the EPO Mar. 21, 2016 (58 pages).
"Response to Communication Pursuant to R161(1) and 162 EPC," for European Patent Application No. 14706247.5, mailed Oct. 30, 2015 and filed with the EPO Dec. 17, 2015 (17 pages).
"Response to Non-Final Office Action," for U.S. Appl. No. 13/284,467, mailed Aug. 6, 2015 and filed with the USPTO Jan. 6, 2016 (6 pages).
"Response to Non-Final Office Action," for U.S. Appl. No. 14/178,869, mailed Oct. 19, 2015 and filed with the USPTO Mar. 15, 2016 (9 pages).
Zhou, Y. et al., "Microstructure Evolution and Mechanical Behavior of MG-10Gd-3Y-0.4Zr Alloy Processed by ECAP at High Temperature," Editor Martyn Alderman et al., Magnesium Technology 2014, TMS (The Minerals, Metals, and Materials Society), 2014, Wiley Publishers, pp. 511-516.
International Preliminary Report on Patentability in International Application No. PCT/US2014/015932, dated Aug. 18, 2015, 9 pages.
International Search Report and Written Opinion in International Application No. PCT/US2014/015932, dated Apr. 9, 2014, 11 pages.
"Notice of Allowance," for U.S. Appl. No. 14/527,317 mailed Sep. 23, 2016 (19 pages).
"Communication Pursuant to Article 94(3) EPC," for European Patent Application No. 07842447.0 mailed Oct. 7, 2016 (4 pages).
"First Office Action," for Chinese Patent Application No. 201480020886.4 mailed Oct. 8, 2016 (19 pages) with English Translation.
"Response to Communication Pursuant to Article 94(3) EPC," for European Patent Application No. 07842447.0 filed with the EPO Dec. 13, 2016 (52 pages).
"Response to Communication Pursuant to Rules 161(1) and 162 EPC," for European Patent Application No. 141796368.0 filed with the EPO Jan. 2, 2017 (12 pages).
Xu, Guang-Liang et al., "Effect of Equal Channel Angular Extrusion on the Microstructure and Mechanical Properties of AZ31 Magnesium Alloy," Material Engineering, vol. 2, Feb. 28, 2011, pp. 69-72.
Erinc, M. et al., "Modified AZ80 Magnesium Alloys for Biomedical Applications," Magnesium Technology, 2010, pp. 641-646.
Erinc, M. et al., "Applicability of Existing Magnesium Alloys as Biomedical Implant Materials," Proceedings of the Symposium held during the TMS Annual Meeting & Exhibition, San Francisco, CA, 2009, pp. 209-214.
"File History," for European Patent Application No. 11752046.0 downloaded from the EPO Jan. 24, 2017 (190 pages).
"File History," for U.S. Appl. No. 13/216,371.
George, S. M. et al., "Molecular Layer Deposition of Organic and Hybrid Organic-Inorganic Polymers," Material Matters, 2008 (3.2), pp. 34-37.
"International Preliminary Report on Patentability," for PCT/US2011/048954 mailed Mar. 12, 2013 (7 pages).
"International Search Report and Written Opinion," for PCT/US2011/048954 mailed Oct. 19, 2011 (10 pages).
Seman, Michael et al., "Self-Limiting Growth of Tantalum Oxide Thin Films by Pulsed Plasma-Enhanced Chemical Vapor Deposition," Applied Physics Letters, 2007, 90: 131504 (3 pages).

\* cited by examiner

BIOERODIBLE MAGNESIUM ALLOY MICROSTRUCTURES FOR ENDOPROSTHESES

TECHNICAL FIELD

This disclosure relates to microstructures for bioerodible magnesium alloys used in endoprostheses and methods of producing those microstructures.

BACKGROUND

Endoprostheses can be used to replace a missing biological structure, support a damaged biological structure, and/or enhance an existing biological structure. Frequently, only a temporary presence of the endoprosthesis in the body is necessary to fulfill the medical purpose. Surgical intervention to remove endoprostheses, however, can cause complications and may not even be possible. One approach for avoiding a permanent presence of all or part of an endoprosthesis is to form all or part of the endoprosthesis out of bioerodible material. The term "bioerodible" as used herein is understood as the sum of microbial procedures or processes solely caused by the presence of endoprosthesis within a body, which results in a gradual erosion of the structure formed of the bioerodible material.

At a specific time, the endoprosthesis, or at least the part of the endoprosthesis that includes the bioerodible material, loses its mechanical integrity. The erosion products are mainly absorbed by the body, although small residues can remain under certain conditions. A variety of different bioerodible polymers (both natural and synthetic) and bioerodible metals (particularly magnesium and iron) have been developed and are under consideration as candidate materials for particular types of endoprostheses. Many of these bioerodible materials, however, have significant drawbacks. These drawbacks include the erosion products, both in type and in rate of release, as well as the mechanical properties of the material.

SUMMARY

A bioerodible endoprosthesis provided herein includes a bioerodible magnesium alloy having a microstructure defined by equiaxed Mg-rich solid solution-phase grains (i.e., alpha-phase grains) having an average grain diameter of less than or equal to 5 microns and second-phase precipitates located in grain boundaries between the equiaxed Mg-rich solid solution-phase grains. The beta-phase precipitates can have an average longest dimension of 0.5 micron or less. Bioerodible magnesium alloys having the microstructures provided herein can have improved mechanical properties suitable for endoprostheses, such as stents.

A method of processing a bioerodible magnesium alloy for endoprostheses provided herein can include the steps of forming an ingot or billet of a magnesium alloy and performing at least one high-strain process on the billet to form the grain and precipitate morphology and size provided herein. In some cases, the processing can include holding the ingot or billet at a temperature above the solvus temperature (e.g., between 400° C. and 450° C.) for at least 2 hours to homogenize the ingot or billet prior to performing the at least one high-strain process. The at least one high-strain process can be an equal-channel high-strain process and can be conducted at a temperature of less than the solvus temperature (e.g., a temperature below 400° C.). In some cases, multiple equal-channel high-strain processes are conducted using subsequently lower temperatures.

Any suitable bioerodible magnesium alloy formulation capable of having magnesium-rich solid solution grains and second-phase precipitates that offer cathodic protection or promote the formation of a protective film to the grains can be used in the bioerodible endoprostheses provided herein. In some cases, the bioerodible magnesium alloy includes aluminum, and aluminum-containing beta-phase precipitates (e.g., $Mg_{17}Al_{12}$) are formed in the grain boundaries between the equiaxed Mg-rich solid solution-phase grains. In some cases, the bioerodible magnesium alloy can include aluminum, zinc, calcium, manganese, tin, neodymium, yttrium, cerium, lanthanum, gadolinium, or a combination thereof. For example, the bioerodible magnesium alloy can include greater than 85 weight percent magnesium, between 5 and 11 weight percent aluminum, between 0.1 and 3.0 weight percent zinc, less than or equal to 0.3 weight percent manganese, and between 0.6 and 1.5 weight percent neodymium.

The endoprosthesis can also include a coating. In some cases, the coating has a maximum thickness of 20 nm. In some cases, the coating includes titanium oxide, aluminum oxide, or a combination thereof. The endoprosthesis can also include a therapeutic agent.

The endoprosthesis can be a stent.

One advantage of an endoprosthesis including a bioerodible magnesium alloy having a microstructure provided herein is that the resulting endoprosthesis' mechanical properties and degradation rate can be tailored to maintain desired mechanical properties over a desired period of time and an optimal bioerosion rate. A bioerodible magnesium alloy having a microstructure provided herein can have improved ductility as compared to similar alloys having different microstructures.

The details of one or more embodiments are set forth in the accompanying drawings and the description below. Other features, objects, and advantages will be apparent from the description and drawings, and from the claims.

DETAILED DESCRIPTION

Figure 1:
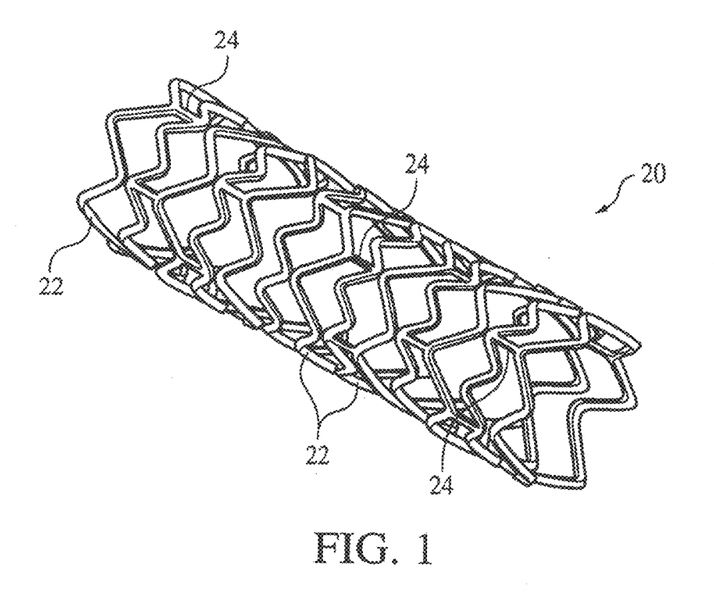
FIG. 1 is a perspective view of a representative stent.

A stent 20, shown in FIG. 1, is an example of an endoprosthesis. Stent 20 includes a pattern of interconnected struts forming a structure that contacts a body lumen wall to maintain the patency of the body lumen. For example, stent 20 can have the form of a tubular member defined by a plurality of bands 22 and a plurality of connectors 24 that extend between and connect adjacent bands. During use, bands 22 can be expanded from an initial, small diameter to a larger diameter to contact stent 20 against a wall of a vessel, thereby maintaining the patency of the vessel. Connectors 24 can provide stent 20 with flexibility and conformability that allow the stent to adapt to the contours of the vessel. Other examples of endoprostheses include covered stents and stent-grafts.

Figure 4:
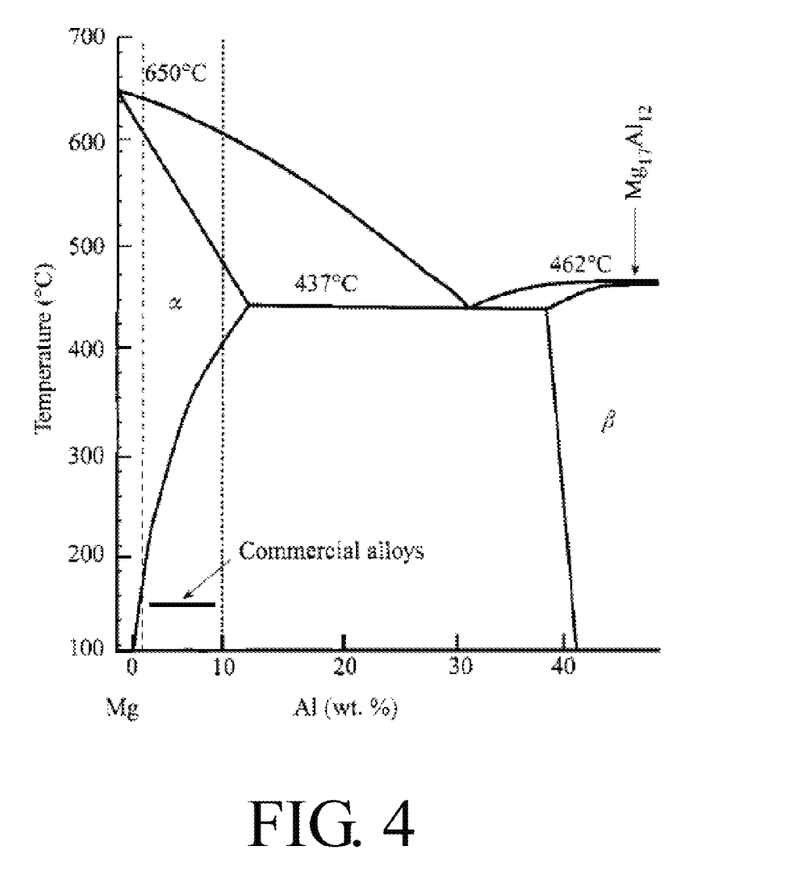
FIG. 4 depicts a phase diagram for a Magnesium-Aluminum alloy.

At least one strut of stent 20 can be adapted to erode under physiological conditions. In some cases, stent 20 is fully bioerodible. Stent 20 can include a bioerodible magnesium-aluminum alloy with relatively small concentrations of additional elements having a microstructure defined by relatively equiaxed magnesium-rich solid solution -phase grains having an average grain diameter of less than or equal to 5 microns (longest dimension in a metallography cross-section plane) and fine discontinuous or continuous second-phase precipitates in grain boundaries between the equiaxed Mg-rich solid solution-phase grains. A phase diagram is shown in FIG. 4.

Figure 3:
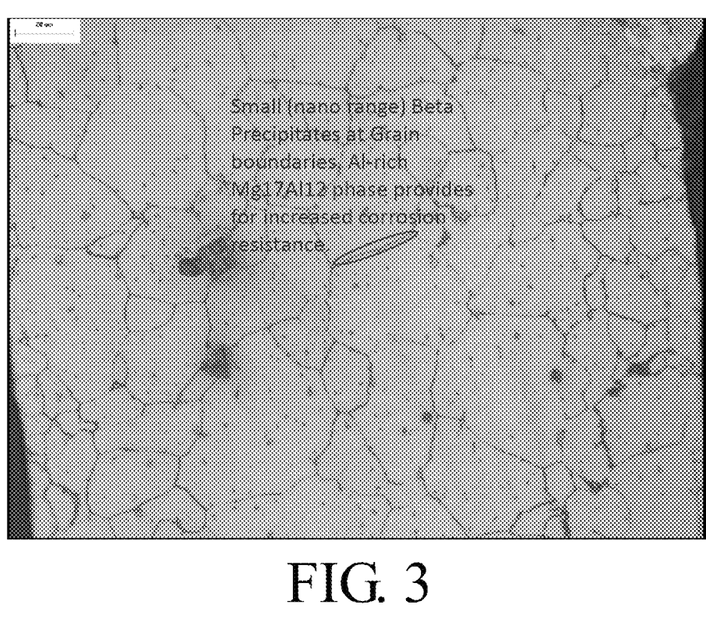
FIG. 3 depicts an exemplary microstructure provided herein.

The beta-phase precipitates can have an average longest dimension of 0.5 micron or less and are predominantly located in grain boundaries rather than within grains (e.g., >50% of the combined area of second-phase precipitates are on grain boundaries in a given prepared metallography cross-section plane examined at 100-300× magnification). For example, FIG. 3 depicts an exemplary microstructure provided herein. As shown in FIG. 3, a majority of the second-phase precipitates (i.e., the beta-phase) are located are located in grain boundaries rather than within the Mg-rich solid solution-phase grains. Magnesium alloys having the microstructures provided herein can have improved mechanical properties suitable for endoprostheses, such as stents.

Although magnesium and magnesium alloys have been explored as candidate materials for bioerodible endoprostheses in the past, the mechanical properties of magnesium and magnesium alloys have presented certain difficulties that make the use of a bioerodible magnesium metal or alloy in certain endoprostheses, such as stents, impractical. In particular, magnesium alloys can have a limited ductility due to a lack of available slip planes in the Hexagonal Close Packed (HCP) crystal lattice. Slip planes can accommodate plastic deformation. Limited ductility can complicate certain uses that rely upon plastic deformation. For example, limited ductility can make stent crimping and stent expansion more complex due to an increased probability of stent fractures during these plastic deformations. Moreover, magnesium alloys typically have a lower tensile strength than iron alloys (such as stainless steel alloys). Bioerodible magnesium alloys having a microstructure provided herein, however, can have improved ductility and tensile strength.

Certain magnesium alloys were tested in order to identify magnesium alloys having suitable bioerosion rates and ductility. For example, L1c and WE43 (described in Table I below) were prototyped and tested as stents, but found to have a bioerosion rate that was too fast when subjected to in-vivo and in-vitro testing. It is possible, however, that a L1c and/or WE43 alloy having a microstructure provided herein would have a suitable bioerodison rate for an endoprosthesis.

Certain modifications of the AZ80 alloy (see Table II below) have also been developed in an attempt to find a magnesium alloy having superior corrosion resistance to that of L1c, but also having sufficient ductility. Although initial mechanical testing of these AZ80 modified alloys showed an improvement in the mechanical and corrosion properties as compared to L1c, AZ80 modified alloy stents cracked and fractured at a nominal expanded diameter.

TABLE II

| Alloy Example | Al | Zn | Mn | Y | Nd | La | Mg |
|---|---|---|---|---|---|---|---|
| AZ80 | 7.5 | 0.5 | 0.2 | — | — | — | Balance |
| AZNd | 7.3 | 0.6 | 0.1 | — | 0.7 | — | Balance |
| AZY | 7.4 | 0.6 | 0.1 | 0.5 | — | — | Balance |
| AZNdY | 7.0 | 0.6 | 0.2 | 0.5 | 0.6 | — | Balance |
| AZM | 7.3 | 0.6 | 0.4 | — | — | — | Balance |
| AZL | 7.0 | 0.5 | 0.2 | — | — | 1.2 | Balance |
| AE82 | 8.0 | 0.5 | 0.2 | 0.5 | 1.0 | — | Balance |

Figure 2A:
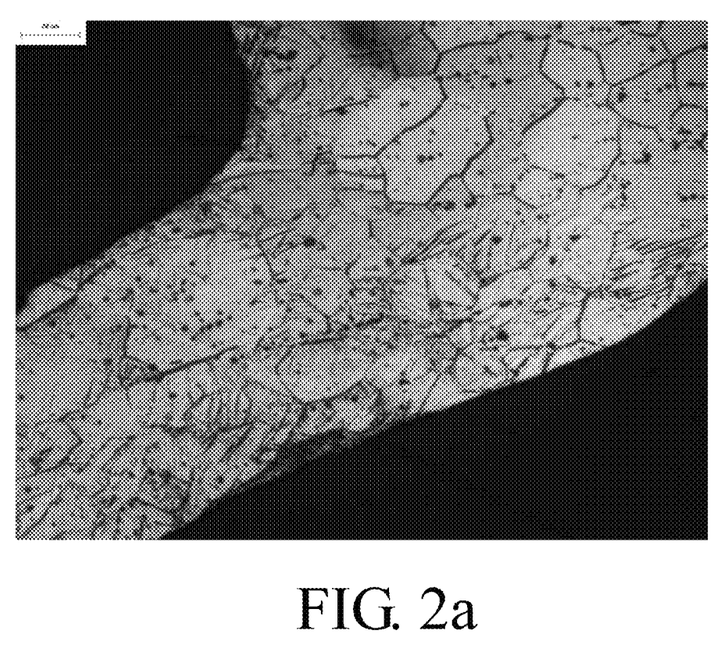
FIGS. 2a and 2b depict metallographic images of etched AZ80 Mod alloy stents.
Figure 2B:
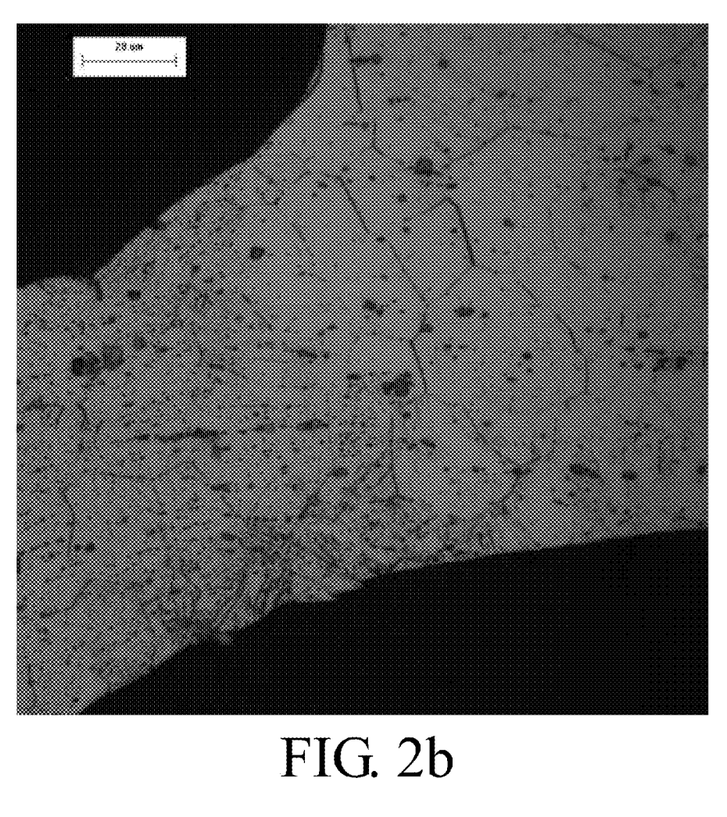

An analysis of the stents identified the presence of large extrinsic intermetallic particles, e.g., oxide inclusions and coarse Mg solid solution grain sizes, which are deleterious to ductility. Low material ductility can result in stent cracking, especially in balloon-expandable stents that are crimped onto a balloon catheter, guided through a long tortuous path, and expanded to fill the diameter of the artery. FIGS. 2A and 2B depict metallographic images of etched AZ82 alloy stents. Referring to FIG. 2A, the circled areas are the tensile and compression areas near the strut peak of this nominally expanded stent. These circled areas show twinning, cracking, and void nucleation. Referring to FIG. 2B, voids are formed during the deformation. Magnesium having the microstructure as shown in FIGS. 2A and 2B can be described as having a coarse grain size with large secondary phase precipitates.

The microstructures and processes provided herein eliminate this root cause of low material ductility and stent cracking by producing raw material alloy with much lower extrinsic inclusion content (or at least much smaller inclusions) and stent material with refined Mg solid solution grain size to randomize grain texture, produce additional slip systems through grain size refinement, and raise the activation energy needed to initiate a crack due to the presence of a tortuous grain boundary network. The microstructures and processes provided herein can be tailored to manifest sufficient ductility in a balloon-expandable stent design such that the Mg alloy stent would allow the stent to be crimped onto a balloon catheter, wiggled through a long tortuous path, and expanded to fill the diameter of the artery without fracturing.

The microstructure of a magnesium alloy is dependent on the processing techniques and parameters. The grains (i.e., crystals) of the alloy can align themselves with their basal planes parallel to the direction of the processing material

TABLE I

| Alloy Ex. | Zn | Zr | Mn | Y | Nd | Ca | Ag | Fe | Other Elements | Mg |
|---|---|---|---|---|---|---|---|---|---|---|
| L1c | 2.87 | ≤0.02 | 0.15 | — | — | 0.22 | 0.10 | 0.0036 | — | Balance |
| WE43 | Not specified | 0.0-1.0 | Not specified | 2.0-6.0 | 1.5-4.5 | Not specified | Not specified | Not specified | 0.5-4.0 of other rare earths metals; 0.0-0.3 Al | Balance | flow, which can result in different mechanical properties in the direction of flow as compared to the a direction perpendicular to the direction of flow. In the case of extruding stent tubing including the alloys of Table II, the resulting tube may have a strong preferred crystal orientation, aligning the basal planes in the extrusion direction, which produces increased ductility in the extrusion direction of the tubing, but less ductility in a direction perpendicular to the extrusion direction. The expansion of a stent, however, relies upon the material having suitable ductility in all directions. A strong grain texture with an unfavorable loading along the c-crystal axis components of the grains causes twinning and void nucleation under lower strains. The twinning with void nucleation shown in FIGS. 2A and 2B can be the initiation of an eventual material failure. Stent tube extrusion may also produce a randomized crystal structure with no preferred orientation, which produces more isotropic mechanical properties, but still suffers from the ductility issues discussed above.

The microstructures provided herein can provide superior ductility and other mechanical properties in multiple directions. As shown in FIG. 3, the grain boundaries are decorated with precipitates. The microstructures provided herein can be characterized in a number of ways. In some cases, the microstructures provided herein, when viewed at a 500× using x-ray diffraction, have no more than 3% by area filled with intermetallic ("IM") particles. In some case, the microstructures provided herein have no more than 2% by area filled with IM particles. In some cases, a maximum IM particle dimension will be 30 microns or less. In some cases, a maximum IM particle dimension will be 20 microns or less, 10 microns or less, 5 microns or less, or 1 micron or less.

The microstructures provided herein can include equiaxed Mg-rich solid solution-phase grains with second-phase precipitates located within smooth and equiaxed alpha-phase-grain boundaries. In some cases, the equiaxed equiaxed Mg-rich solid solution-phase grains have an average grain size of 20 microns or less, 15 microns or less, 10 microns or less, 7.5 microns or less, 5 microns or less, or 4 microns or less. In some cases, the equiaxed Mg-rich solid solution-phase grains have an average grain size of between 0.1 microns and 10 microns, of between 0.5 microns and 5 microns, or between 1 micron and 4 microns. In some cases, at least 90% by volume of the beta phase particles can be found along alpha phase grain boundaries. In some cases, the average beta phase individual particle diameter or longest dimension is 5 microns or less, 3 microns or less, 1 micron or less, or 0.5 micron or less. In some cases, the average beta phase individual particle diameter or longest dimension is between 0.05 microns and 5 microns, between 0.1 microns and 3 microns, or between 0.2 microns and 1 micron. The microstructure provided herein can have a reduced number of twin bands. In some cases, less than 15% of the alpha grains will have twin bands. In some cases, the number of alpha grains having twin bands can be less than 10%, less than 5%, or less than 1% when the stent is cut and crimped.

Microstructures provided herein can enhance ductility. The microstructures provided herein can overcome the basal plane alignment by randomizing grain orientations and result in isotropic mechanical properties. Finer grains also yield increased grain boundary areas, which can provide more grain boundary slip. Refinement of precipitate diameter may also allow additional grain boundary slip. Moreover, a homogenous dispersion of beta-phase precipitates along the grain boundaries can maximize precipitation strengthening and corrosion resistance. In some cases, the precipitates can be substantially centered on the grain boundary but be larger than the width of the grain boundary. For example, the aluminum content of a magnesium alloy can react to form corrosion resistant oxides at exposed grain boundaries to protect each grain from corrosion. Moreover, smaller grains, each protected by the formation of corrosion resistant oxides, can further slow the corrosion of the overall structure of the bioerodible magnesium alloys provided herein. Additionally, the beta-phase precipitates can be fine enough so that they do not significantly impede ductility.

A tubular body (e.g., stent tubing material) made from AZNd alloy of the aim formulation shown in Table III, below, having a microstructure provided herein can have an elastic modulus of between 39 and 44 GPa, a 0.2% Offset Yield Strength of between 150 and 350 MPa, an ultimate tensile strength of between 225 and 400 MPa, a tensile reduction in area (RIA) of between 30% and 80%. In some cases, stent tubing material provided herein can have a tensile RIA of between 45% and 80%. In some cases, stent tubing material provided herein can maintain its initial elastic modulus, Yield Strength, ultimate tensile strength, and a tensile RIA within +/−10% after storage of the tubing for 180 days at a temperature of between 20° C. and 25° C. and a relative humidity of less than 30%.

TABLE III

| | | Al | Zn | Mn | Nd | Si | Cu (ppm) | Fe (ppm) |
|---|---|---|---|---|---|---|---|---|
| Batch 1 | Specification | 8 | 0.5 | <0.2 | 1 | — | <25 | <25 |
| | XRF | 8.80 | 0.55 | 0.10 | 0.68 | 0.031 | 23 | 24 |
| | DES | 7.26 | 0.59 | 0.10 | 0.66 | 0.012 | 29 | 35 |
| Batch 2 | Specification | 8 | 0.5 | <0.2 | 1 | — | <25 | <25 |
| | XRF | | | | | | | |
| | DES | 8.2 | 0.43 | 0.23 | 0.65 | ? | ? | ? |
| Batch 3 | Specification | 8 | 0.5 | — | 1 | — | <25 | <25 |
| | XRF | 7.3 | 0.32 | 0.024 | 0.63 | 0.02 | <10 | 26 |
| | DES | | | | | | | |

Bioerodible magnesium alloys having a microstructure provided herein can be polished to have a smooth surface finish. In some cases, an endoprosthesis provided herein can have a surface including a bioerodible magnesium alloy having a surface roughness $R_a$ of less than 0.5 microns, less than 0.4 microns, less than 0.3 microns, or less than 0.2 microns. Bioerodible magnesium alloys having microstructure provided herein can have improved corrosion resistance, which can provide a slower bioerosion rate. A stent body of a bioerodible magnesium alloy having a microstructure provided herein can have an in-vitro corrosion penetration rate of less than 200 µm/year after a period of 28 days of continuous immersion in non-flowing, agitated Simulated Body Fluid (agitated at 60 rpm) at 37° C. where the Simulated Body Fluid ("SBF") is present in an amount of at least 10 times the initial volume of the stent material. The ingredients of SBF, which are added to water, are shown in Table 4.

TABLE 4

SBF Ingredients

| Chemical | Mass/Volume |
|---|---|
| NaCl | 5.403 g |
| NaHCO$_3$ | 0.504 g |
| Na$_2$CO$_3$ | 0.426 g |
| KCl | 0.225 g |
| K$_2$HPO$_4$•3H$_2$O | 0.230 g |
| MgCl$_2$•6H$_2$O | 0.311 g |
| 0.2M NaOH | 100 mL |
| HEPES | 17.892 g |
| CaCl$_2$ | 0.293 g |
| Na$_2$SO$_4$ | 0.072 g |

In some cases, the magnesium alloy includes aluminum. In some cases, Mg$_{17}$Al$_{12}$ beta phases can precipitate in a bioerodible magnesium alloy provided herein. Mg$_{17}$Al$_{12}$ beta phases can be less cathodic than phases that form from other alloy systems, which can provide improved corrosion resistance relative to alloys having more cathodic precipitates. The precipitates can be more noble than the Mg grains and form a corrosion-resistant barrier along grain boundaries and thereby protect the grain interiors as a "grain coating." Aluminum can also form native oxide layers along grain boundaries, which can act as a protective layer for the grains and delay the onset of intergranular corrosion. Smaller grain sizes can also reduce the corrosion rate because corrosion must re-initiate past the protective oxide layer for each grain corroded.

The microstructure provided herein can be formed by the following material treatments: (a) solution treating a billet to solutionize the second-phase precipitates that originally formed during solidification of the alloy; (b) controlled cooling after solutionizing to form a distribution of fine discontinuous or continuous precipitates along grain boundaries; and (c) thermomechanical deformation of the material after or during cooling to refine the Mg-rich solid solution grain size and produce a substantially equiaxed grain morphology.

For example, a billet of a bioerodible magnesium alloy can be formed or machined into a solid or hollow rod, homogenized, subjected to a high-strain process to refine the microstructure, and then shaped or machined into stent tubing from which the stent is manufactured into final dimensions (e.g., the dimensions of a stent body).

Billets including a bioerodible magnesium alloy can be made using any suitable process. For example, the billet can be of bioerodible magnesium alloy having a diameter of between 2 centimeters and 1 meter. In some cases, an ingot of a desired bioerodible magnesium alloy can be made by conventional melting and solidification in a mold (liquid casting), thixomolding (semi-solid processing) or powder metallurgy (solid-processing). The ingot can then be machined to the desired dimensions of the billet which will serve as the feedstock for subsequent processing and shaping. In some cases, a billet of a desired bioerodible magnesium alloy can be formed without additional machining process. To form an endoprosthesis (e.g., a stent body) out of the billet, the billet can be converted into a rod or hollow tube having a smaller diameter. In some cases, the ingot or billet is converted into a rod or hollow tube after the ingot or billet is homogenized. In some cases, the rod or hollow tube can have an outer diameter of between 1 centimeter and 6 centimeters. In the case of a stent, a hollow tube of a bioerodible magnesium alloy having a microstructure provided herein can then be further reduced in diameter and cut to form individual stent bodies, including fenestrations between stent struts. In some cases, the stent struts can have a width to thickness ratio of less than 1.2. In some cases, the thickness of the hollow tube and the stent struts can be between 80 microns and 160 microns.

An ingot or billet, in some cases, can be made by thixomolding the elements of the bioerodible magnesium alloy. Thixomolding involves mixing solid constituents into a portion of the composition that is in a liquid phase and then cooling the mixture to reach a fully solid state. Thixomolding can reduce the number and size of brittle inter-metallic (IM) particles in the alloy. For example, thixomolding can use a machine similar to an injection mold. Room temperature magnesium alloy chips and chips of the other alloy constituents can be fed into a heated barrel through a volumetric feeder. The heated barrel can be filled with an inert gas (e.g., argon) to prevent oxidation of the magnesium chips. A screw feeder located inside the barrel can feed the magnesium chips and other alloy constituents forward as they are heated into a semi-solid temperature range. For example, the mixture can be heated to a temperature of about 442° C. The screw rotation can provide a shearing force that can further reduce the size of IM particles. Once enough slurry has accumulated, the screw can move forward to inject the slurry into a steel die having the shape of an ingot or billet.

An ingot or billet, in some cases, can be made by combining the elements of the bioerodible magnesium alloy using powder metallurgy. Powder metallurgy involves the solid-state sintering of elemental or pre-alloyed powder particles. Using fine powders in a sintering process can avoid the formation of coarse IM particles. For example, fine powders of magnesium and other alloying constituents can be blended into a homogenous mixture, pressed into a desired shape (e.g., the shape of the ingot or billet), and heated while compressed to bond the powders together. Sintering can be conducted in an inert atmosphere (e.g., argon) to avoid oxidation of the magnesium.

An ingot or billet including all of the desired elements of a bioerodible magnesium alloy can be homogenized to reduce elemental concentration gradients. The ingot or billet can be homogenized by heating the ingot or billet to an elevated temperature below the liquidus temperature of the alloy and holding the ingot or billet at that temperature for period of time sufficient to allow elemental diffusion within the ingot or billet to reduce elemental concentration gradients within the ingot or billet.

Homogenizing the ingot or billet can solutionize intermetallic (IM) second-phase precipitate particles, because the homogenization temperature is in excess of the phase boundary (solvus temperature) between the high-temperature single, solid phase (alpha) and two-phase field boundary on the Mg—Al phase diagram. A follow-on solutioning treatment at the same or similar position within the phase diagram can be used in some cases to refine the precipitate structure. For example, a follow-on solutioning treatment can be used if the homogenization treatment cooling was not controlled sufficiently to tailor the second-phase precipitate size and location. In some cases, the ingot or billet is cooled rapidly after holding the ingot or billet at the elevated temperature in order to form relatively fine IM second-phase precipitates. For example, the ingot or billet can be cooled from the elevated hold temperature via force gas cooling or liquid quenching. The ingot or billet can be homogenized in an inert atmosphere (e.g., in an argon atmosphere) or open atmosphere so long as surface oxides are removed. In some cases, the ingot or billet provided herein can be homogenized at a temperature of between 400° C. and 450° C. In some cases, the ingot or billet is held at a temperature of between 400° C. and 450° C. for at least 2 hours, at least 3 hours, or at least 4 hours. In some cases, the hold time at an elevated temperature is between 4 hours and 24 hours. For example, a bioerodible magnesium alloy ingot having a diameter of about 15 centimeters can be heated to a temperature of 440° C. for 6 hours to homogenize the ingot, followed by quenching the ingot in a cooled argon gas stream.

An ingot or billet can be subjected to one or more high-strain processes to refine the microstructure into a microstructure provided herein. In some cases, the high-strain process(es) can include one or more equal-channel high-strain processes. Equal-channel high-strain processes include Equal-Channel Angular Extrusion ("ECAE") and Equal-Channel Angular Pressing ("ECAP"). ECAE is an extrusion process that produces significant deformation strain without reducing the cross sectional area of the piece. ECAE can be accomplished by extruding the alloy (e.g., a billet of the alloy) around a corner. For example, a billet of a bioerodible magnesium alloy provided herein can be forced through a channel having a 90 degree angle. The cross section of the channel can be equal on entry and exit. The complex deformation of the metal as it flows around the corner can produce very high strains. In some cases, an ingot can be machined into a billet having the exact dimensions of the channel of an ECAE die prior to an ECAE process. Because the cross section can remain the same, the billet can be extruded multiple times with each pass introducing additional strain. With each ECAE process, the orientation of the billet can be changed to introduce strain along different planes. In some cases, an ECAE die can include multiple bends. For example, FIGS. 5A-5D depict a variety of ECAE dies.

The ingot or billet provided herein can be extruded through one or more ECEA dies (e.g., as depicted in FIGS. 5A-5D) at temperatures lower than a homogenization temperature. Multiple equal-channel high-strain extrusions can be performed at subsequently lower temperatures. The equal-channel high-strain processes can yield a fine grain size with fine beta-phase precipitates (i.e., IM particles) that are primarily located along the grain boundaries. In some cases, the dynamic recrystallization of the grain refinement caused by successive equal-channel high-strain extrusions at declining temperatures can introduce more strain into the material and result in finer grain sizes as compared to cold working and annealing steps. In some cases, an ingot or billet is subjected to at least two ECAE processes at two different sequentially-lower temperatures. In some cases, an ingot or billet is subjected to at least three ECAE processes at different sequentially-lower temperatures.

For example, a billet including a magnesium-aluminum alloy can be processed through two ECAE processes, with the first ECAE process occurring at a higher temperature than the second ECAE process. Each process can occur through a simple ECAE die have a single 90° corner, such as that depicted in FIG. 5A. The first ECAE process can be conducted at a temperature of between 250° C. and 400° C. to allow good diffusion of aluminum to the grain boundaries where it can precipitate in the form of $Mg_{17}Al_{12}$ beta phases. The $Mg_{17}Al_{12}$ beta phases can be spherical and can have a diameter of about 1 micron or less. Other beta phases can also move towards the grain boundaries and precipitate there, depending on the particular alloy composition. The first ECAE process can result in a microstructure having an average grain diameter of 15 microns or less. A second ECAE process can be done at a temperature of between 150° C. and 300° C. The second ECAE process can further refine the grain sizes and avoid coarsening. Because the first ECAE process can be used to form Al-containing beta phases near the grain boundaries, a lower temperature ECAE process can still allow diffusion of Al- to the grain boundaries which form additional secondary phase precipitate. The second ECAE process can produce an average grain diameter of 5 microns or less. The beta-phase precipitates can have an average diameter of 1 micron or less.

Figures 5A, 5B, 5C, 5D:
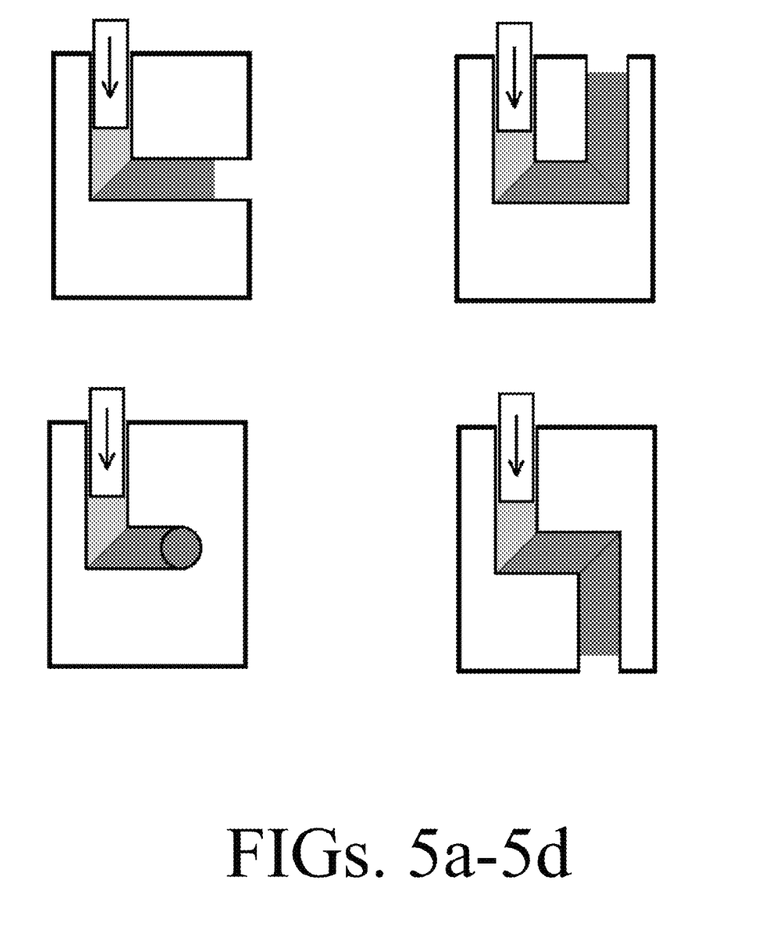
FIGS. 5a-5d depicts exemplary Equal-Channel Angular Extrusion dies.

In the ECAE process shown in FIG. 5A, an ingot or prior-worked billet 30a is extruded through a channel 31a including two channel portions 32a, 33a of substantially identical cross-sectional areas having the respective centerlines thereof disposed at an angle 35a. As shown, angle 35a can be about 90°. In some cases, angle 35a can be between 45° and 170°, between 50° and 160°, between 60° and 135°, between 70° and 120°, between 80° and 100°, or between 85° and 95°. Billet 30a can have any appropriate cross section and machined to provide a snug fit into entry channel portion 32a. In some cases, billet 30a can have a circular cross sectional shape. A ram 38a can force billet 30a through channel 31a using an appropriate extrusion ram pressure. The strain imposed on billet 30a is a function of angle 35a.

In the ECAE process shown in FIG. 5B, an ingot or prior-worked billet 30b is extruded through a channel 31b, including three channel portions 32b, 33b, and 34b of substantially identical cross-sectional areas having the respective centerlines thereof disposed at angles 35b and 36b. As shown, angles 35b and 36b can be about 90°. In some cases, angles 35b and 36b can be between 45° and 170°, between 50°and 160°, between 60° and 135°, between 70° and 120°, between 80° and 100°, or between 85° and 95°. Billet 30b can have any appropriate cross section and machined to provide a snug fit into entry channel portion 32b. In some cases, billet 30b can have a circular cross sectional shape, in other cases a square cross-sectional shape. A ram 38b can force billet 30b through channel 31b using an appropriate extrusion ram pressure. The strain imposed on billet 30b is a function of angles 35b and 36b.

In the ECAE process shown in FIG. 5C, an ingot or prior-worked billet 30c is extruded through a channel 31c, including three channel portions 32c, 33c, and 34c of substantially identical cross-sectional areas having the respective centerlines thereof disposed at angles 35c and 36c. As shown, angles 35c and 36c can be about 90° and in separate planes. In some cases, angles 35c and 36c can be between 45° and 170°, between 50° and 160°, between 60° and 135°, between 70° and 120°, between 80° and 100°, or between 85° and 95°. Billet 30c can have any appropriate cross section and machined to provide a snug fit into entry channel portion 32c. As shown, billet 30c can have a circular cross sectional shape. A ram 38c can force billet 30cthrough channel 31c using an appropriate extrusion ram pressure. The strain imposed on billet 30c is a function of angles 35c and 36c. Moreover, having the channel portions 32c, 33c, and 34c in different planes can impart shear forces along different planes in a single pass.

In the ECAE process shown in FIG. 5D, an ingot or prior-worked billet 30d is extruded through a channel 31d, including three channel portions 32d, 33d, and 34d of substantially identical cross-sectional areas having the respective centerlines thereof disposed at angles 35d and 36d. As shown, angles 35d and 36d can be about 90° and in opposite directions. In some cases, angles 35d and 36d can be between 45° and 170°, between 50° and 160°, between 60° and 135°, between 70° and 120°, between 80° and 100°, or between 85° and 95°. Billet 30d can have any appropriate cross section and machined to provide a snug fit into entry channel portion 32d. For example, billet 30d can have a circular cross sectional shape. A ram 38d can force billet 30d through channel 31d using an appropriate extrusion ram pressure. The strain imposed on billet 30d is a function of angles 35d and 36d.

The billet can be formed into a rod or hollow tube having a reduced outer diameter after one or more high-strain processes. Tube or rod drawing from the billet can occur in multiple steps, with optional intermediate and final annealing steps, to reduce the diameter. The drawing and annealing processes can be controlled to preserve the microstructure formed in the one or more high-strain processes. In some cases, the material is annealed at a temperature of less than 300° C. In some cases, the material is annealed at a temperature of between 150° C. and 300° C., between 150° C. and 250° C., or between 150° C. and 200° C. Annealing steps can be used to allow recovery with limited recrystallization and avoid grain growth or changes in precipitate volume fraction and morphology Annealing steps can also maintain a homogenous dispersion of beta-phase precipitates at the grain boundaries.

Individual stent bodies can then be cut, including cutting fenestrations between stent struts, using any suitable technique. For example, the fenestrations can be cut using a laser.

Bioerodible magnesium alloys having a microstructure provided herein can include magnesium alloyed with any suitable combination of additional elements. In some cases, a bioerodible magnesium alloy having a microstructure provided herein can include aluminum. In some cases, a bioerodible magnesium alloy having a microstructure provided herein can include zinc. In some cases, a bioerodible magnesium alloy having a microstructure provided herein can include calcium. In some cases, a bioerodible magnesium alloy having a microstructure provided herein can include tin. In some cases, a bioerodible magnesium alloy having a microstructure provided herein can include manganese. In some cases, a bioerodible magnesium alloy having a microstructure provided herein can include neodymium. For example, a bioerodible magnesium alloy having a microstructure provided herein can include at least 85 weight percent magnesium, between 5 and 11 weight percent aluminum, between 0.1 and 3 weight percent zinc, and between 0.05 and 0.3 weight percent manganese, between 0.6 and 1.5 weight percent neodymium, up to 100 ppm copper, and up to 175 ppm iron. Other possible bioerodible magnesium alloys include those listed in Tables I and II above. Examples of other suitable bioerodible magnesium alloys can be found in U.S. Patent Application Publication No. 2012/0059455, which is hereby incorporated by reference in its entirety, particularly the sections describing particular bioerodible magnesium alloys.

A bioerodible magnesium alloy having a microstructure provided herein can include a variety of different additional elements. In some cases, the bioerodible magnesium alloy includes less than 5 weight percent, in sum, of elements other than magnesium, aluminum, zinc, and manganese. In some cases, the bioerodible magnesium alloy includes less than 2 weight percent, in sum, of elements other than magnesium, aluminum, zinc, and manganese. The bioerodible magnesium alloy can consist essentially of magnesium, aluminum, zinc, manganese, and neodymium. As used herein, "consisting essentially of" means that the alloy can also include impurities normally associated with the commercially available forms of the constituent elements in amounts corresponding to the amounts found in the commercially available forms of the constituent elements. In some cases, the potential impurity elements of iron, copper, nickel, gold, cadmium, bismuth, sulfur, phosphorous, silicon, calcium, tin, lead and sodium are each maintained at levels of less than 1000 ppm. In still other embodiments, the potential impurity elements of iron, copper, nickel, cobalt, gold, cadmium, bismuth, sulfur, phosphorous, silicon, calcium, tin, lead and sodium are each maintained at levels of less than 200 ppm. Iron, nickel, copper, and cobalt have low solid-solubility limits in magnesium and can serve as active cathodic sites and accelerate the erosion rate of magnesium within a physiological environment. In still other embodiments, each of iron, nickel, copper, and cobalt is maintained at levels of less than 50 ppm. For example, each of the first five alloys listed in Table II has no more than 35 ppm of iron.

Bioerodible magnesium alloys provided herein can optionally include one or more rare earth metals. In some cases, the bioerodible magnesium alloy includes between 0.1 and 1.5 weight percent of a first rare earth metal. In some cases, the first rare earth metal is yttrium, neodymium, lanthanum, or cerium. The bioerodible magnesium alloy can also include between 0.1 and 1.5 weight percent of a second rare earth metal. For example, a bioerodible magnesium alloy provided herein can include about 0.5 weight percent yttrium and 0.6 weight percent neodymium. In some cases, the bioerodible magnesium alloy includes three or more rare earth metals. In some cases, the total amount of rare earth metals within the bioerodible magnesium alloy is maintained at a level of less than 10.0 weight percent. In some cases, the total amount of rare earth metals within the bioerodible magnesium alloy is maintained at a level of less than 2.5 weight percent.

A coating can be applied over a bioerodible magnesium alloy of an endoprosthesis provided herein. For example, a stent provided herein can include a stent body formed of a bioerodible magnesium alloy including a microstructure provided herein and a coating overlying the surface of the stent body. A coating can slow or delay the initial degradation of the bioerodible magnesium alloy upon placement within a physiological environment by serving as a temporary barrier between the Mg alloy and the environment. For example, delaying the bioerosion processes can allow the body passageway to heal and a stent to become endothelialized (surrounded by tissues cells of the lumen wall) before the strength of the stent is reduced to a point where the stent fails under the loads associated with residing within a body lumen (e.g., within a blood vessel). When an endothelialized stent fragments, the segments of the stent can be contained by the lumen wall tissue and are thus less likely to be released into the blood stream. Endothelialization can also block the oxygen-rich turbulent flow of the blood stream from contacting the endoprosthesis, thus further reducing the erosion rate of the endoprosthesis. In some case, a stent provided herein can include a coating that includes titanium oxide, aluminum oxide, or a combination thereof. Examples of suitable coatings can be found in U.S. Patent Application Publication No. 2012/0059455, which is hereby incorporate by reference in its entirety, particularly the sections describing coatings formed by atomic layer deposition.

The stent can optionally include a therapeutic agent. In some cases, the coating can include a therapeutic agent. In some cases, the coating can include a polymer (e.g., a bioerodible polymer). For example, a drug-eluting polymeric coating can be applied to the stent body provided herein. In some cases, a stent provided herein can be essentially polymer-free (allowing for the presence of any small amounts of polymeric materials that may have been introduced incidentally during the manufacturing process such that someone of ordinary skill in the art would nevertheless consider the coating to be free of any polymeric material). The therapeutic agent may be any pharmaceutically acceptable agent (such as a drug), a biomolecule, a small molecule, or cells. Exemplary drugs include anti-proliferative agents such as paclitaxel, sirolimus (rapamycin), tacrolimus, everolimus, biolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, lipids, and compounds have a molecular weight of less than 100 kD. Exemplary cells include stem cells, progenitor cells, endothelial cells, adult cardiomyocytes, and smooth muscle cells.

A stent provided herein can include one or more imaging markers. Imaging markers can assist a physician with the placement of the stent. Imaging markers can be radiopaque marks to permit X-ray visualization of the stent.

Stent 20 can be configured for vascular, e.g., coronary and peripheral vasculature or non-vascular lumens. For example, it can be configured for use in the esophagus or the prostate. Other lumens include biliary lumens, hepatic lumens, pancreatic lumens, and urethral lumens.

Stent 20 can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some cases, a peripheral stent can have an expanded diameter of from about 4 mm to about 24 mm. In certain embodiments, a gastrointestinal and/or urology stent can have an expanded diameter of from about 6 mm to about 30 mm. In some cases, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., see U.S. Pat. No. 6,290,721).

Non-limiting examples of additional endoprostheses that can include a bioerodible magnesium alloy including a microstructure provided herein include stent grafts, heart valves, and artificial hearts. Such endoprostheses are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

All publications, patent applications, patents, and other references mentioned herein are incorporated by reference herein in their entirety.

Still further embodiments are within the scope of the following claims.

What is claimed is:

1. A method of processing a bioerodible magnesium alloy containing at least 85 weight percent magnesium for an endoprosthesis comprising:
    forming an ingot or billet comprising a magnesium alloy, the magnesium alloy comprising magnesium and one or more alloying elements;
    performing at least one strain process on the ingot or billet to form a microstructure comprising equiaxed Mg-rich solid solution-phase grains having an average grain diameter of less than or equal to 5 microns and continuous or discontinuous second-phase precipitates in grain boundaries between the equiaxed Mg-rich solid solution-phase grains, the second-phase precipitates having an average longest dimension of 0.5 micron or less, wherein less than 15% of the equiaxed Mg-rich solid solution-phase grains have twin bands; and
    forming a rod or hollow tube from the ingot or billet, including performing an intermediate annealing step at a temperature of between 150° C. and 200° C.

2. The method of claim 1, further comprising holding the ingot or billet at a temperature of between the solvus and liquidus boundaries of the phase diagram for at least 2 hours to homogenize the ingot or billet before performing the at least one strain process on the ingot or billet.

3. The method of claim 1 wherein the at least one strain process is an equal-channel strain process preformed at a temperature of less than 400° C.

4. The method of claim 3, wherein the ingot or billet is processed through at least two equal-channel strain processes at different temperatures, wherein a first equal-channel strain process occurring at a first time is performed at a higher temperature than a second equal-channel strain process occurring at a second time after the first time, wherein the first equal-channel strain process is performed at a temperature of between 250° C. and 400° C. and the second equal-channel strain process is performed at a temperature of between 150° C. and 300° C.

5. The method of claim 1, wherein the second-phase precipitates are primarily centered upon the gran boundaries and do not extend into a Mg-rich solid solution phase grain interior by more than 1 micron from the grain boundary when viewed at 200-500× magnification on a metallography plane.

6. The method of claim 1, wherein the equiaxed Mg-rich solid solution phase grains have an average grain diameter of less than or equal to 1 micron and the second-phase precipitates have an average longest dimension of 0.2 microns or less.

7. The method of claim 1, wherein less than 5% of the equiaxed Mg-rich solid solution-phase grains have twin bands.

8. The method of claim 1, wherein the bioerodible magnesium alloy includes beta-phase precipitates outside the grain boundaries, wherein at least 50% of the total amount of beta-phase precipitates are located in grain boundaries between the equiaxed Mg-rich solid solution-phase grains.

9. The method of claim 1, wherein the bioerodible magnesium alloy includes beta-phase precipitates outside the grain boundaries, wherein at least 65% of the total amount of beta-phase precipitates are located in grain boundaries between the equiaxed Mg-rich solid solution-phase grains.

10. The method of claim 1, wherein the bioerodible magnesium alloy includes beta-phase precipitates outside the grain boundaries, wherein at least 80% of the total amount of beta-phase precipitates are located in grain boundaries between the equiaxed Mg-rich solid solution-phase grains.

11. The method of claim 1, wherein the alloy has an elastic modulus of between 39 GPa and 44 GPa, a 0.2% offset yield strength of between 150 MPa and 350 MPa, an ultimate tensile strength of between 250 MPa and 400 MPa, and a tensile reduction in area of at least 30%.

12. The method of claim 1, wherein the second-phase grain boundary precipitates comprise $Mg_{17}Al_{12}$.

13. The method of claim 1, wherein the bioerodible magnesium alloy comprises zinc, calcium, manganese, neodymium, tin, yttrium, cerium, lanthanum, gadolinium, or a combination thereof.

14. The method of claim 1, wherein the bioerodible magnesium alloy comprises between 0.1 and 3.0 weight percent zinc, up to 0.3 weight percent manganese, and between 0.6 and 1.5 weight percent neodymium, and balance magnesium.

15. The method of claim 1, wherein the endoprosthesis is a stent comprising a plurality of struts, wherein the struts have a width to thickness ratio of less than 1.2.

16. The method of claim 1, wherein the endoprosthesis has a surface finish having an $R_a$ surface roughness of less than 0.5 microns.

17. The method of claim 1, wherein the fully manufactured non-sterile or sterile finished product bare bioerodible magnesium alloy endoprosthesis has a mass loss of less than 10% after 28 days of continuous immersion in non-flowing, agitated Simulated Body Fluid at 37° C., where the Simulated Body Fluid has a volume of at least 10 times an initial volume of the endoprosthesis.

18. The method of claim 1, the magnesium alloy comprising between 5 and 11 weight percent aluminum.

* * * * *